US00PP20929P2

(12) United States Plant Patent
Jones

(10) Patent No.: US PP20,929 P2
(45) Date of Patent: Apr. 13, 2010

(54) ***SALVIA* PLANT NAMED 'CATHEDRAL SKY BLUE'**

(50) Latin Name: *Salvia farinacea*
Varietal Denomination: CATHEDRAL SKY BLUE

(76) Inventor: Steve Jones, 1800 N. Tyler Ave., South El Monte, CA (US) 91733

( * ) Notice: Subject to any disclaimer, the term of this patent is extended or adjusted under 35 U.S.C. 154(b) by 0 days.

(21) Appl. No.: 12/283,304

(22) Filed: Sep. 10, 2008

(51) Int. Cl.
*A01H 5/00* (2006.01)

(52) U.S. Cl. ..... Plt./475

(58) Field of Classification Search ..... Plt./475
See application file for complete search history.

*Primary Examiner*—Kent L Bell

(57) ABSTRACT

A new and distinct *Salvia* cultivar named 'CATHEDRAL SKY BLUE' is disclosed, characterized by having distinctive light lavender flowers, a compact, very well-branched plant habit, shortened panicle and early, flowering. The new variety is a *Salvia*, normally produced as an outdoor garden or container plant.

1 Drawing Sheet

Figure 1:
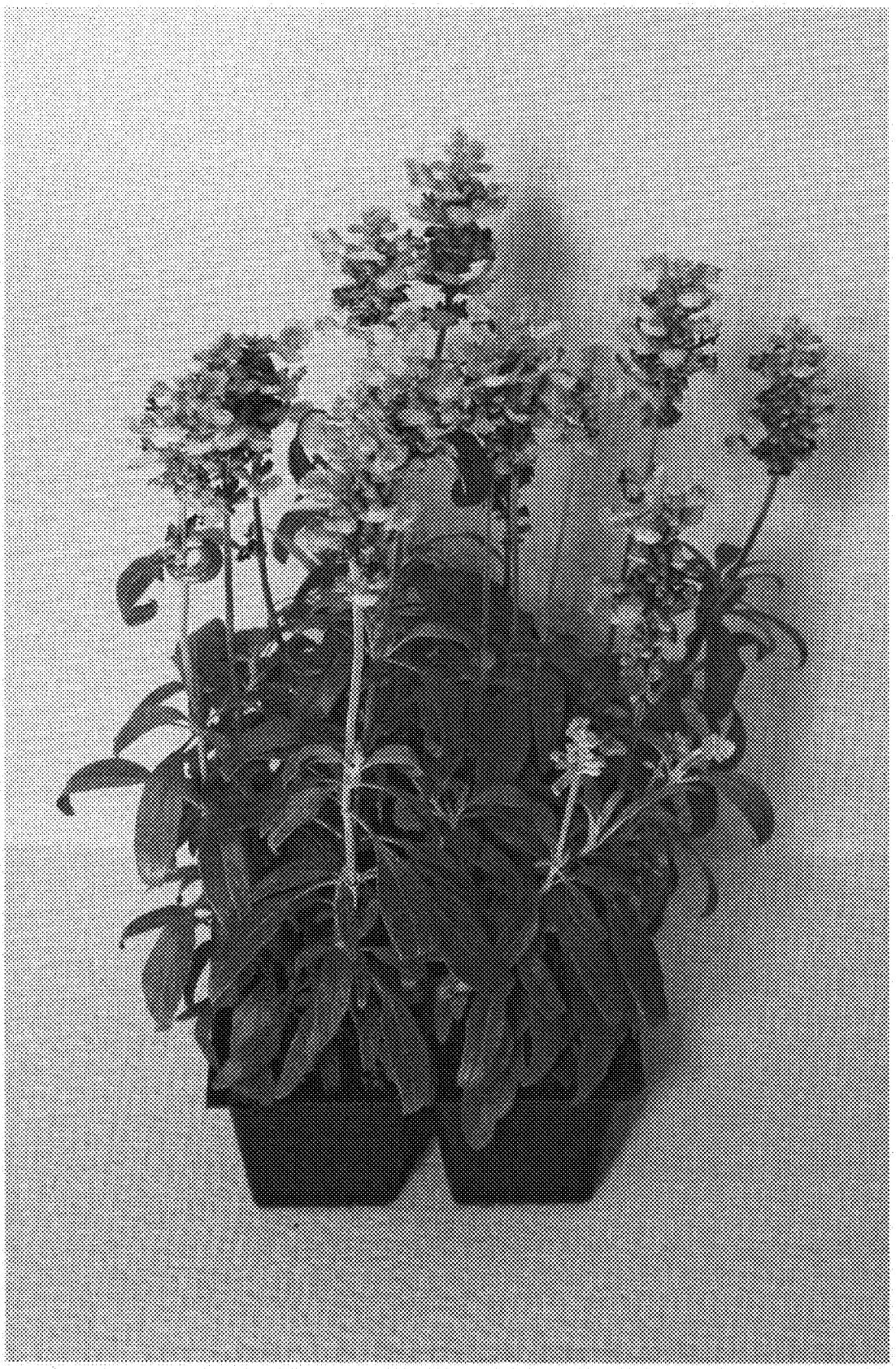

Latin name of the genus and species: *Salvia farinacea.*
Varietal denomination: 'CATHEDRAL SKY BLUE'.

BACKGROUND OF THE INVENTION

The new cultivar was discovered as a spontaneous whole plant mutation by the inventor, Steve Jones. The parent variety is the unpatented, variety *Salvia farinacea* 'Signum'. The new variety was discovered as a naturally occurring, whole plant mutation January 2000, by the inventor in a commercial planting of approximately 100,000 plants of *Salvia farinacea* 'Signum' in Quillota, Chile.

Asexual reproduction of the new cultivar 'CATHEDRAL SKY BLUE' by vegetative cuttings was first performed January 2000, at a commercial greenhouse in Quillota, Chile and has shown that the unique features of this cultivar are stable and reproduced true to type on successive generations.

SUMMARY OF THE INVENTION

The cultivar 'CATHEDRAL SKY BLUE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CATHEDRAL SKY BLUE' These characteristics in combination distinguish 'CATHEDRAL SKY BLUE' as a new and distinct *Salvia* cultivar:

1. Compact plant habit.
2. Distinctly unique soft lavender flowers.
3. Shortened panicle.
4. Early flowering.

PARENT COMPARISON

Plants of the new cultivar 'CATHEDRAL SKY BLUE' are similar to plants of the parent, *Salvia farinacea* 'Signum' in most horticultural characteristics, however, plants of the new cultivar 'CATHEDRAL SKY BLUE' are shorter. Additionally, flowers of the parent variety are dark blue, whereas, the new variety produces distinct, soft lavender flowers, and have a longer panicle.

COMMERCIAL COMPARISON

Plant of the new cultivar are best compared to the commercial variety *Salvia farinacea* 'Victoria' an unpatented and widely available variety. Plants of the new variety are significantly shorter and more compact. 'CATHEDRAL SKY BLUE' also blooms earlier than 'Victoria.' Additionally, flowers of the new variety are lighter colored than 'Victoria'.

BRIEF DESCRIPTION OF THE PHOTOGRAPH

The accompanying photograph in FIG. 1 illustrates in full color a typical plant of 'CATHEDRAL SKY BLUE' grown in a greenhouse, in Lompoc, Calif. in a commercial 6 cell pack. Age of the plant photographed is 12 weeks from an unrooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'CATHEDRAL SKY BLUE' plants grown in a greenhouse in Lompoc, Calif. The growing temperature ranged from 20° C. to 28° C. The greenhouse is un-shaded, giving bright, normal sunlight conditions. Measurements and numerical values represent averages of typical plant types.

Botanical classification: *Salvia farinacea* cultivar 'CATHEDRAL SKY BLUE'.

PROPAGATION

Time to initiate roots: About 5–8 days at approximately 25° C.
Root description: Fine, densely fibrous.
Time to produce a rooted cutting: About 21 days at 25° C.

PLANT

Growth habit: Upright annual.
Pot size of plant described: 6 cell pack.
Height: Approximately 23 cm.
Plant spread: Approximately 18 cm.
Growth rate: Rapid.
Branching characteristics: Free-branching, Approximately 4 primary branches.
Length of primary lateral branches: Approximately 8 cm.
Diameter of lateral branches: Approximately 0.4 cm
Quantity of lateral branches: About 16.
Stem:
*Color.*—Near RHS Green 139 D.
*Pubescence.*—Very slight pubescence.
Internode length: Approximately 2.8 cm.
Age of plant described: Approximately 12 weeks from an unrooted cutting.

FOLIAGE

Leaf:
*Arrangement.*—Opposite, mainly. Many upper nodes have multiple, single leaves emerging from same node, in an opposite pattern.
*Quantity.*—Approximately 18 per main branch.
*Average length.*—Approximately 5.8 cm.
*Average width.*—Approximately 1.1 cm.
*Shape of blade.*—Lanceolate.
*Apex.*—Acute.
*Base.*—Attenuate.
*Attachment.*—Stalked.
*Margin.*—Slightly dentate.
*Texture of top surface.*—Matte.
*Pubescence.*—None.
*Color.*—Young foliage upper side: Near RHS Yellow-Green 147A. Young foliage under side: Near RHS Yellow-Green 146B. Mature foliage upper side: Near RHS Green 138A. Mature foliage under side: Near RHS Green 138B.
*Venation.*—Type: Pinnate. Venation color upper side: Near RHS Yellow-Green 144A. Venation color under side: Near RHS Yellow-Green 145A.
*Petiole.*—Average Length: Approximately 1 cm. Diameter: Approximately 0.1 cm. Color: Near Yellow-Green 145A.

FLOWER

Natural flowering season: Begins flowering 6 weeks from planting a rooted cutting. Flowering continues from early Spring through late Summer.
Inflorescence type and habit: Flowers arranged in verticillasters on spikes.
Flower longevity on plant: Individual flowers last 5 days on the plant. Each spike lasts approximately 6 weeks with flowers.
Quantity of flowers: About 30 buds and 12 fully opened flowers per lateral branch, at one time; about 4 blooming spikes per plant.
Inflorescence size:
*Diameter.*—Approximately 3.2 cm.
*Height.*—Approximately 8 cm.
Peduncle:
*Length.*—7–9 cm.
*Diameter.*—0.8 cm.
*Color.*—Near RHS Green 138D.
*Orientation.*—Upright, straight.
*Strength.*—Strong.
Corolla:
*Petal arrangement.*—The corolla is sympetalous and typically bilabiate with 2 small, highly fused lobes forming an upper lip and 4 larger highly fused lobes forming a lower lip.
*Margin.*—Slightly scalloped.
*Tip shape.*—Upper lip tip retuse, lower lip tip rounded with scallops.
*Length.*—Upper lip Approximately 0.5 cm, lower lip Approximately 1.1 cm.
*Width.*—Upper lip Approximately 0.4 cm, lower lip Approximately 1 cm.
*Petal quantity.*—One upper lip and one lower lip with four lobes. Upper lips are entirely fused at base.
*Petal apex shape.*—Obtuse.
*Texture.*—Upper lip has short, feather-like hairs, lower lip is smooth and hairless.
*Aspect.*—90° to stem.
*Petaloids.*—Shape: Spatulate. Length: Approximately 0.3 cm. Width: Approximately 0.2 cm. Base: Cuneate. Apex: Obtuse. Texture: Glabrous. Color: Near RHS Violet-Blue 91C.
*Color.*—
Petals: When opening: Upper surface: Apex Near RHS Violet-Blue 95C, base Near RHS Violet-Blue 95D. Lower surface: Near RHS Violet-Blue 91 C. Fully opened: Upper surface: Near RHS Violet-Blue 91B. Lower surface: Near RHS Violet-Blue 91D with 93D at apex.
Bud:
*Shape.*—Ovoid.
*Length.*—Approximately 0.4 cm.
*Diameter.*—Approximately 0.2 cm.
*Color.*—Near RHS Violet-Blue 92D.
Calyx:
*Length.*—Approximately 0.6 cm.
*Diameter.*—Approximately 0.4 cm.
*Shape.*—Tubular.
*Sepals.*—Shape: Quantity per flower; 2, fused to form a tube. Apex: Obtuse. Length: Approximately 0.6 cm. Color, both inside and outside of tube: Immature: Near RHS Violet-Blue 91D. Mature: Near RHS Violet-Blue 91B.
*Bracts.*—Quantity: 2 at the base of each flower. Shape: Ovate. Base: Cuneate. Tip: Accuminate Texture: Lightly pubescent.

REPRODUCTIVE ORGANS

Stamens:
*Number.*—2.
*Filament length.*—Approximately 0.3 cm.
Anthers:
*Shape.*—Very narrowly elliptic.
*Length.*—Approximately 1 mm.
*Color.*—Near RHS Violet-Blue 91A.
*Pollen*: Color: Near RHS Yellow 12A. Quantity: Moderate.
Pistil:
*Number.*—1.
*Length.*—Approximately 0.8 cm.

*Style.*—Length: Approximately 0.6 cm Color: Near RHS Violet-Blue 91D.

*Stigma.*—Shape: Two-parted, cleft Color: Near RHS Purple 79B. Ovary color: Near RHS Yellow-Green 1B.

OTHER CHARACTERISTICS

Seeds and fruits: Not observed and not commercially important.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'CATHEDRAL SKY BLUE' as herein illustrated and described.

* * * * *